United States Patent [19]
Dadson et al.

[11] Patent Number: 5,141,492
[45] Date of Patent: Aug. 25, 1992

[54] METHOD AND APPARATUS FOR PERFORMING PERITONEAL DIALYSIS

[76] Inventors: Joseph E. Dadson, 7 Harrow Smith Place, Richmond Hill, Ontario, Canada, L4E 2E1; Mahesh Agarwal, 7 Grant's Place, Markham, Ontario, Canada, L3S 2W2

[21] Appl. No.: 707,025

[22] Filed: May 29, 1991

[51] Int. Cl.⁵ .............................................. A61M 1/28
[52] U.S. Cl. ........................................ 604/28; 604/29
[58] Field of Search ........................... 604/27, 28, 29; 177/225, 174, DIG. 6

[56] References Cited

U.S. PATENT DOCUMENTS

| | | | |
|---|---|---|---|
| 4,096,859 | 6/1978 | Agarwal et al. | 604/29 X |
| 4,224,604 | 9/1980 | Angst | 177/DIG. 6 |
| 4,994,026 | 2/1991 | Fecondini | 604/29 |

*Primary Examiner*—John J. Wilson
*Assistant Examiner*—Jeffrey A. Smith
*Attorney, Agent, or Firm*—Shoemaker and Mattare, Ltd.

[57] ABSTRACT

An apparatus for carrying out peritoneal dialysis includes a central manifold, a receptacle for waste dialysate, means for supporting and heating a plurality of fresh dialysate bags, a first conduit connecting the manifold with the patient catheter, a second conduit for connecting the manifold with the receptacle, and a plurality of additional conduits connecting the manifold individually with a plurality of fresh dialysate bags. The individual conduits can be selectively closed by clamping means controlled by an electronic control, and the latter has an automatic mode which cycles the apparatus through (a) a fill/dwell phase in which the contents of one of the fresh dialysate bags flows into the patient's peritoneum cavity by gravity and remains there, and (b) a drain phase which allows waste dialysate in the patient's peritoneum cavity to drain by gravity into the receptacle. The steps (a) and (b) are repeated for all of the bags until they have been used up. A safety provision is provided to determine whether a sufficient quantity of dialysate has drained from the patient's cavity during the drain phase. If not, the apparatus is shut down.

10 Claims, 8 Drawing Sheets

METHOD AND APPARATUS FOR PERFORMING PERITONEAL DIALYSIS

This invention relates to a new automatic machine for peritoneal dialysis for both hospital and home use.

BACKGROUND OF THIS INVENTION

Automatic Peritoneal Dialysis (APD) machines have been around for a number of years. The introduction of these APD machines helped to advance peritoneal dialysis modality. There are two major types of APD machines. The most complicated versions are the Automatic Fluid Proportioning units. Because of their large size and the operational complexities these machines are gradually being phased out of clinical use.

The less complex APD machines are the cyclers. Functionally most of the cyclers have five independent levels or fluid stages. By gravity, dialysate (dialysis solution) is sequentially passed from one level to another.

The dialysate originates from the first, highest stage which holds the fresh sterile solution bulk. From there the dialysate is transferred to the second, next lower stage where the solution is measured and heated. The next lower stage (third) is the patient. He/she receives the measured solution from the second stage. The fourth stage is the drain bag used to collect the spent dialysate from the patient. The final, lowest stage receives the waste dialysate from the drain bag.

One variation of the cycler fluid level arrangement is where the first stage is located below the second stage and dialysate is transferred from the first stage to the second stage by means of a pump. All cyclers otherwise work according to the same general principle: they accommodate 4 to 12 bags of prepared sterile dialysate, select a predetermined volume of solution from the "bulk" solution bags, heat the dialysate up to near body temperature and deliver this solution to the patient. After a preset time (dwell time), the dialysate is drained out of the patient and into a drain bag were it is weighed. The spent dialysate is discarded from the drain bag into a final drain which could be a waste bag. Typical prior art cycler machines are represented by Agarwal et al U.S. Pat. No. 4,096,859, Lasker et al U.S. Pat. No. 3,872,863 and Davis et al U.S. Pat. No. 4,585,436.

The major forms of peritoneal dialysis (PD) therapy are
1) The Manual Peritoneal Dialysis
2) The Continuous Ambulatory Peritoneal Dialysis (CAPD)
3) The Intermittent Peritoneal Dialysis (IPD)
4) The Continuous Cyclic Peritoneal Dialysis (CCPD).

Therapies 1 and 2 are performed without the need of a machine. The contents of the solution bags are individually and manually delivered to the patient and then drained from the patient accordingly. Therapies 3 and 4 require the use of a cycler. The contents of more than one solution bag are mixed together before delivery to the patient. Of all the PD therapies the most popular one is the CAPD. It is used mainly by patients who have been trained to perform their treatments at their respective homes.

Originally, CAPD that was done using a single tubing set was simple and less costly. However, the high infection rate associated with CAPD made it less attractive. The other shortcoming of CAPD is the fact that once on CAPD, a patient is committed to perform 4 or more fluid exchanges per day, every day. Each fluid exchange may take as much as one hour. Consequently patient "fatigue", which leads to poor aseptic dialysis technique and a high infection rate, is very common. Hence CCPD was introduced as an alternate modality. The limitations of the CCPD programme (machine and tubing complexities, higher cost of tubing sets, non-portable equipment etc.) did not make it easy for most patients to consider CCPD as a better alternative to CAPD.

GENERAL DESCRIPTION OF THIS INVENTION

In order to further advance the PD modality, either a new method or a better machine for performing dialysis has to be introduced. Of these two options, the simplest is the introduction of a new type of Automatic Peritoneal Dialysis Machine which combines all the major advantages of the present four main PD therapies. Better still would be a new and unique APD machine which is capable of performing any one of: Manual PD, CAPD, IPD and CCPD. The present invention is directed to the latter solution, namely a superior and simpler APD machine that can be used to perform all of the four major PD modalities.

More particularly, this invention provides an apparatus for carrying out peritoneal dialysis on a patient whose peritoneum cavity communicates with a patient catheter, the apparatus comprising:
(1) a manifold,
(2) a receptacle for waste dialysate,
(3) a plurality of fresh dialysate bags,
(4) support means supporting said plurality of fresh dialysate bags,
(5) heating means for heating said dialysate bags on said support means,
(6) a first conduit for connecting the manifold with the patient catheter,
(7) a second conduit for connecting said manifold with said receptacle,
(8) at least two further conduits connecting the manifold individually with each of said fresh dialysate bags,
(9) clamping means for selectively closing at least said second and said further conduits, and
(10) electronic control means for controlling said clamping means, the electronic control means having an automatic mode in which the control means causes the apparatus to cycle through the following phases:
 a) a fill/dwell phase in which, for a first predetermined time, the first conduit and one of said at least two further conduits are both open while the remaining conduits are closed, thus allowing dialysate to enter the patient's peritoneum cavity by gravity and remain there, so long as the vertical level of the dialysate bags is above that of the patient, and
 b) a drain phase in which, for a second predetermined time, the first and second conduits are both open while the remaining conduits are closed, thus allowing waste dialysate to drain by gravity from the patient's peritoneum cavity to said receptacle, so long as the vertical level of the patient is above that of the receptacle, said steps a) and b) repeating for another fresh dialysate bag, and so on until all such bags have been used;
(11) safety means for determining whether a sufficient quantity of dialysate has drained from the patient's peritoneum cavity during the drain phase, and for passing such information to said electronic control means, said electronic control means being such as not to advance to the next fill/dwell phase if an insufficient quantity of dialysate has drained, and
(12) selection means allowing a user to select the first and second predetermined times.

Further, this invention provides a method for carrying out peritoneal dialysis on a patient whose peritoneum cavity communicates with a patient catheter, the method comprising the steps:
a) providing an apparatus which includes
 a manifold,
 a receptacle for waste dialysate,
 support means for supporting a plurality of fresh dialysate bags,
 heating means for heating dialysate bags on said support means,
 a first conduit for connecting the manifold with the patient catheter,
 a second conduit for connecting said manifold with said receptacle,
 at least two further conduits for connecting the manifold individually with a plurality of fresh dialysate bags, and
 clamping means for selectively closing said conduits;
b) using electronic control means for controlling said clamping means in an automatic mode in which the control means causes the apparatus to cycle through the following phases:
 1) a fill/dwell phase in which, for a first predetermined time, the first conduit and one of said at least two further conduits are both open while the remaining conduits are closed, whereby dialysate enters the patient's peritoneum cavity by gravity and remains there, so long as the vertical level of the dialysate bags is above that of the patient, and
 2) a drain phase in which, for a second predetermined time, the first and second conduits are both open while the remaining conduits are closed, whereby waste dialysate drains by gravity from the patient's peritoneum cavity to said receptacle, so long as the vertical level of the patient is above that of the receptacle,
c) determining whether a sufficient quantity of dialysate has drained from the patient's cavity during the drain phase, and passing such information to said electronic control means, the electronic control means being such as not to advance to the next fill/dwell phase if an insufficient quantity of dialysate has drained, and
d) repeating said steps 1) and 2) for another fresh dialysate bag, and so on until all such bags have been used.

In a preferred embodiment of this invention, the safety means mentioned above includes weighing means for weighing the receptacle and for supplying a signal when the weight of the receptacle exceeds a predetermined amount, along with means for passing the signal to the electronic control means.

GENERAL DESCRIPTION OF THE DRAWINGS

One embodiment of this invention is illustrated in the accompanying drawings, in which like numerals denote like parts throughout the several views, and in which:
FIG. 1 is a schematic drawing of the prior art over which this invention is an improvement;
FIG. 2 is a schematic drawing of the system of the present invention;
FIG. 3 is a perspective view of an apparatus suitable for carrying out the invention;
FIGS. 4a, 4b and 4c are front, side and rear elevational views of the major control component of the system of this invention;
FIG. 5 is a perspective view of the clamping mechanism forming part of the control unit of FIG. 4a;
FIG. 6 is a logic diagram showing the flow of steps for operating the apparatus of this invention, in either an automatic or a manual mode;
FIG. 7 is a vertical sectional view through a portion of the control housing illustrating the method for sensing the weight of a drainage receptacle bag; and
FIGS. 8a and 8b are a somewhat schematic elevational and frontal views, respectively, of a position sensor for use with the cam clamping mechanism.

DETAILED DESCRIPTION OF THE DRAWINGS

Figure 1:
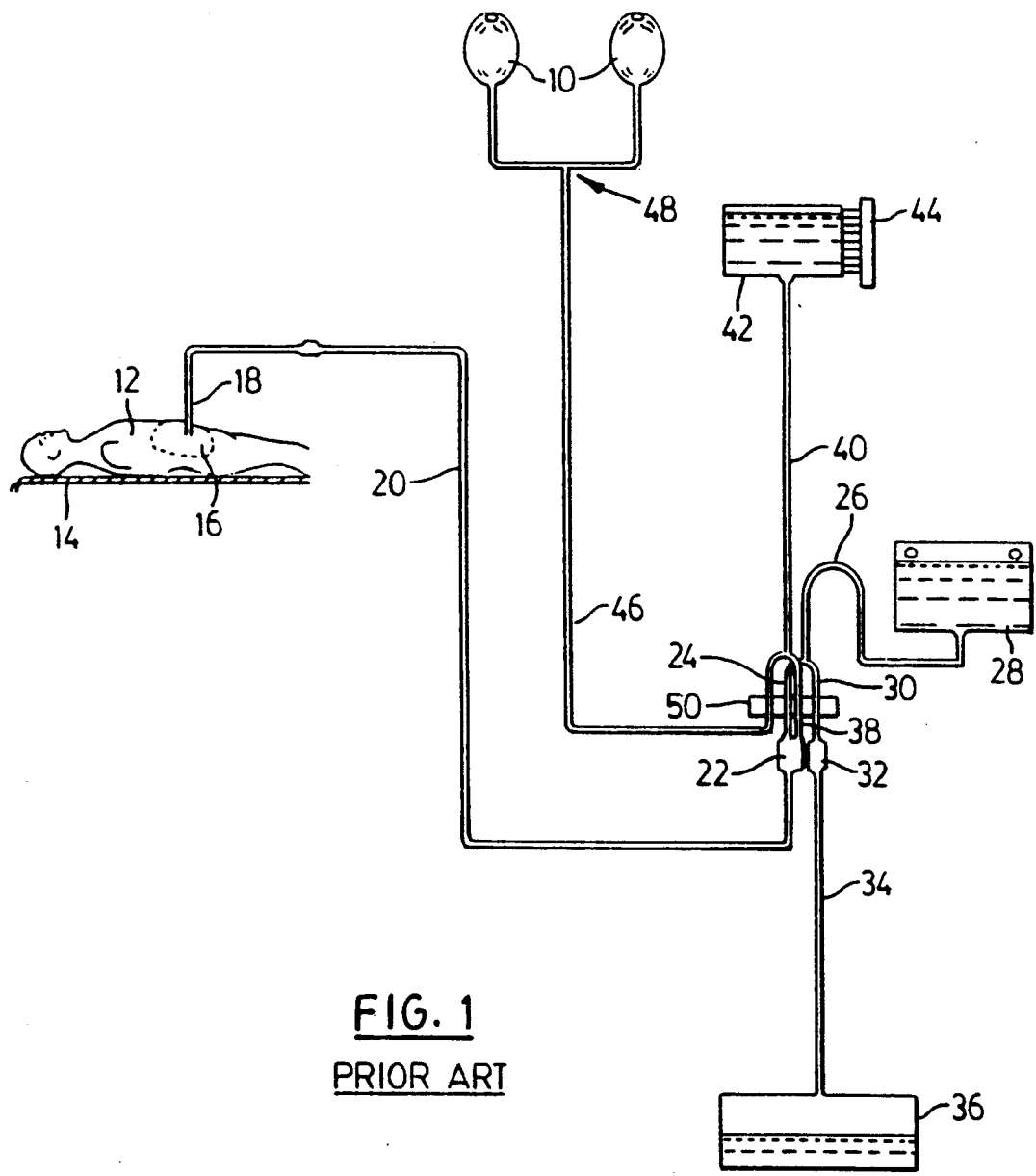

Attention is first directed to FIG. 1, which is illustrative of the prior art. In FIG. 1, one or a plurality of fresh dialysate bags 10 are supported from suitable means (not illustrated) at a vertical height which is situated above the level of a patient 12 lying on a bed or suitable support 14. The patient 12 has a peritoneum cavity 16, and a catheter 18 permanently connected to the patient 12 is in turn connected to a conduit 20 which leads to a first chamber 22. Extending from the chamber 22 is a conduit 24 which branches into a conduit 26 leading to a drain bag 28 suspended on a weighing scale (not illustrated), and a conduit 30 which communicates with a further chamber 32 from which a drain conduit 34 extends to a waste receptacle 36.

The chamber 22 has a further conduit extending upwardly and branching into a conduit 40 leading to a receptacle 42 adapted to be warmed by a heater 44, and a further conduit 46 leading to a branch location 48 which in turn is connected to the plurality of bags 10. As can be seen, all of the conduits 24, 30, 38 and 46 pass through a clamping system 50 which includes clamping fingers or the like which are suitably controlled.

The prior art cycler operates in the following manner. After the patient 12 is hooked into the system, it is common for a "drain" phase to take place, in case the patient has excess dialysate from a previous treatment session that should be drained away before the new session begins. Accordingly, the pathway from the conduit 20 through conduit 24 and conduit 26 to the drain bag 28 is opened, while the conduits 30 and 38 remain closed. Once the patient has fully drained, the new session begins by having dialysate from the fresh bags 10 drain down through the conduit 46 and up along conduit 40 to the receptacle 42. The heater 44 is turned on, and the dialysate in the receptacle 42 rises to approximately body temperature. Then, the pathway from the receptacle 42, along the conduits 40, 38 and 20 is opened (all others in the clamping device 50 being closed) to allow the liquid in the receptacle 42 to pass into the patient's peritoneum cavity 16 by gravity. Note that the bags 10 are at the highest level, the receptacle 42 is at the next highest level, the patient is next in order, the drain bag 28 follows the patient in descending vertical order, and the waste receptacle 36 is at the bottom.

When an appropriate quantity of the solution in the receptacle 42 has drained into the peritoneum cavity 16 of the patient 12, clamping device 50 closes the conduits 24 and 38, and opens conduits 30 and 46. A "dwell" phase then follows during which dialysis takes place with impurities passing from the patient's blood into the dialysate in his peritoneum cavity 16. During this phase, the contents of the drain bag 28 drain out through conduits 26, 30 and 34 into the waste receptacle 36. When a suitable length of time has passed, the pathway connecting conduit 20 with conduit 26 is opened (conduits 30 and 38 being closed), so that the waste dialysate in the peritoneum cavity 16 of the patient 12 can pass into the drain bag 28. The scale weighs the bag 28 to ensure that, when the dialysate stops flowing, a sufficient quantity has been accumulated in the drain bag 28. Failure to attain a predetermined weight in the drain bag 28 will mean that, for some reason, dialysate is being retained in the peritoneum cavity 16 at the patient 12, and typically an alarm would sound if this condition is reached.

When the waste dialysate from the peritoneum cavity 16 of the patient 12 has passed into the drain bag 28, the pathways 26, 30 and 34 are opened, with all others being closed, in order to allow the liquid in the drain bag 28 to drain down into the waste receptacle 36.

Figure 2:
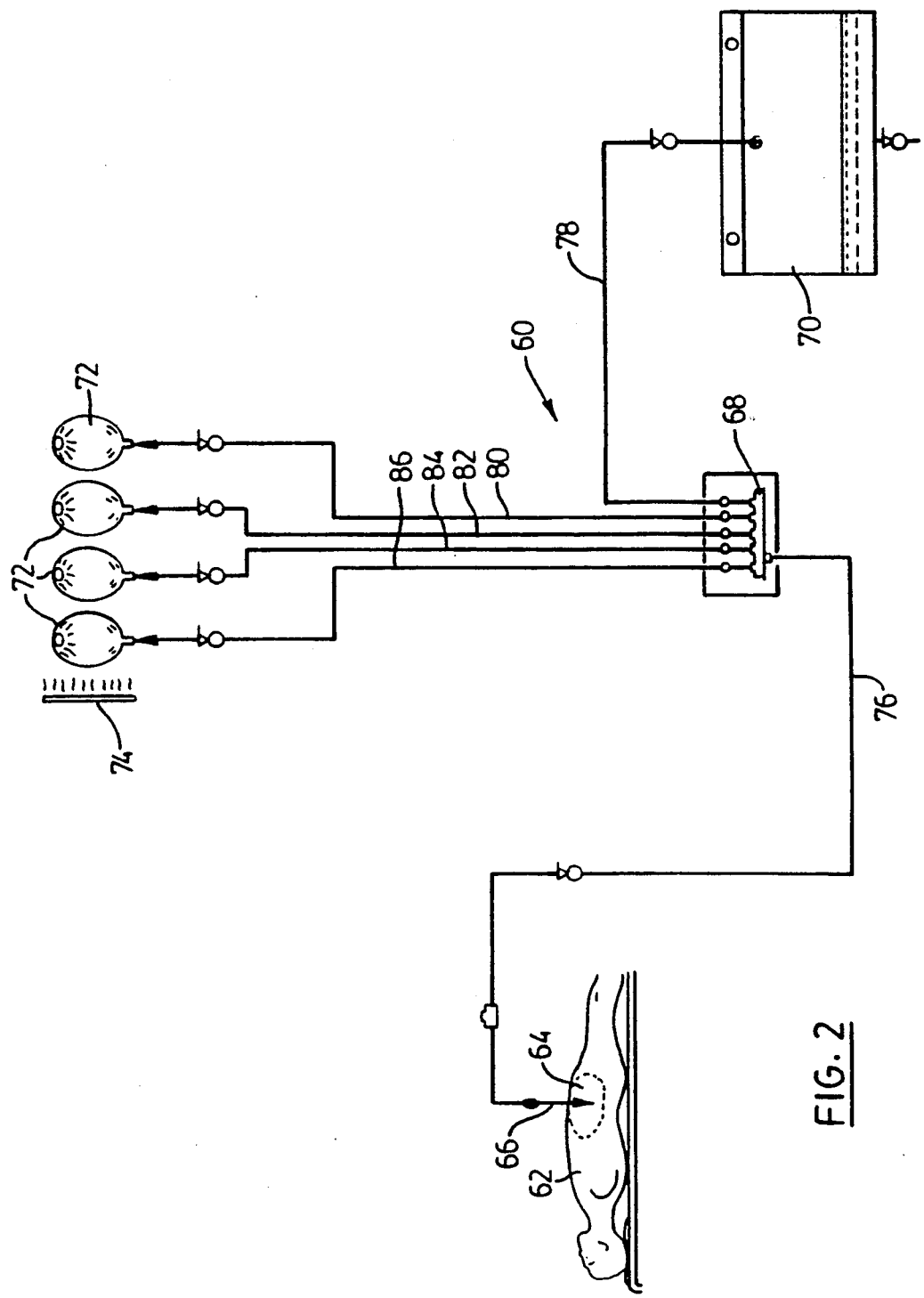

Attention is now directed to FIG. 2, which shows the essential components of the apparatus of this invention. The major principle of fluid delivery in this system is gravity. Functionally, the present invention has only three stages compared to the five stages of the regular cycler machine described with reference to FIG. 1. The fluid stage levels shown in FIG. 2 include an upper level where the fresh dialysate bags are located, an intermediate level where the patient is located, and a combination of scale and waste bag is at the lowermost level. It is important to realize that the normal "heater-scale" stage shown by the numerals 42 and 44 in FIG. 1 is completely eliminated in the present system. Furthermore the prior art combination of drain bag 28 and waste receptacle 36 are combined together to form a single container. Because of these alterations with respect to the prior art, the tubing set system of the present invention is greatly simplified. As a result, the present invention (1) reduces plastic material (conservation of material);
(2) reduces cost of tubing sets;
(3) simplifies tubing set network; and
(4) reduces machine set up time.

Attention is now directed more closely to FIG. 2, for a quick overview of the main components of the system of this invention.

Essentially, FIG. 2 shows an apparatus 60 for carrying out peritoneal dialysis on a patient 62 whose peritoneum cavity 64 communicates with a patient catheter 66. The apparatus includes a manifold 68 which may take the form of a chamber or cavity, a receptacle 70 for receiving waste dialysate, support means (not shown in FIG. 2) for supporting a plurality of fresh dialysate bags 72, heating means 74 for heating the dialysate bags 72, a first conduit 76 for connecting the manifold 68 with the patient catheter 66, a second conduit 78 for connecting the manifold 68 with the receptacle 70, at least two further conduits for connecting the manifold 68 individually with a plurality of fresh dialysate bags (these conduits being four in number in this embodiment, and being identified by the numerals 80, 82, 84 and 86), clamping means (not seen in FIG. 2) for selectively closing the conduits, and an electronic control means (not shown in FIG. 2) for controlling the clamping means. The electronic means has an automatic mode in which it causes the apparatus 60 to cycle through the following phases:

a) a fill/dwell phase in which, for a first predetermined time, the first conduit 76 and a conduit to one of the fresh dialysate bags are both open while the remaining conduits are closed, thus allowing dialysate to enter the patient's peritoneum cavity by gravity and remain there, so long as the vertical level of the dialysate bags is above that of the patient, and b) a drain phase in which, for a second predetermined time, the first and second conduits 76 and 78 are both open while the remaining conduits are closed, thus allowing waste dialysate to drain by gravity from the patient's peritoneum cavity to said receptacle, so long as the vertical level of the patient is above that of the receptacle. Steps a) and b) are then repeated for another fresh dialysate bag and so on until all of the dialysate bags have been used.

The apparatus further includes a safety means for determining whether a sufficient quantity of dialysate has drained from the patient's cavity during the drain phase, and for passing such information to the electronic control means, the latter being such that it will not advance to the next fill/dwell phase if an insufficient quantity of dialysate has drained. In the embodiment of the invention shown in FIG. 2, the safety means includes weighing means for weighing the receptacle 70, and for supplying a signal when the weight of the receptacle 70 exceeds a predetermined amount. The signal is then communicated to the electronic control means. If the electronic control means does not receive that signal within a predetermined amount of time, the automatic mode will be terminated and the apparatus will not advance to the next fill/dwell phase.

The apparatus 60 further includes means to allow the user to select the quantity of liquid in the receptacle 70 at which the weighing means will supply the signal, and also to select the first and second predetermined times mentioned above.

It is stressed again that all three of the fluid levels (the fresh dialysate bags at the top, the patient in the middle and the receptacle 70 at the bottom) are directly and separately joined to the single manifold 68. This is quite unlike the prior art illustrated in FIG. 1, in which all of the dialysate bags are connected together to a single conduit 46.

Figure 3:
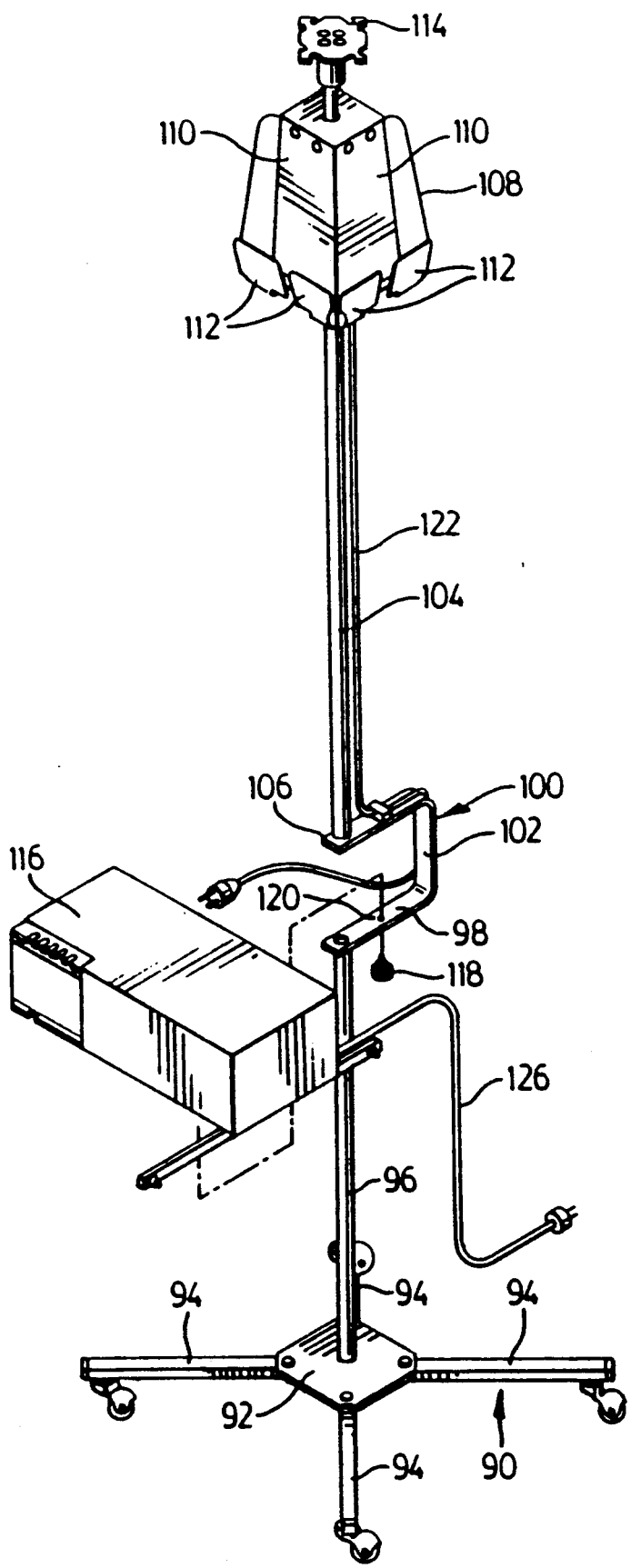

Attention is now directed to FIG. 3, which illustrates a practical apparatus that can perform the procedure described above with respect to FIG. 2. In FIG. 3, the numeral 90 designates a base portion having a central plate 92 and four arms 94 at 90° intervals, each having a caster at its distal end. A first vertical post portion 96 is secured to and extends vertically upwardly from the plate 92 of the base portion 90, the first vertical post portion 96 being secured, at its top end, to one arm 98 of a U-shaped intermediate portion 100, such that the base 102 of the U-shape is displaced laterally away from the post portion 96. The apparatus further includes a second vertical post portion 104 secured to the other arm 106 of the U-shaped portion 100 in such a way that the second vertical post portion is in substantial vertical alignment with the first post portion 96. At the top of the second vertical post portion 104 is located support means 108. The support means 108 has four trapezoidal side walls 110 which converge upwardly, each having a pair of retention flanges 112 which can grip a fresh dialysate bag from underneath. A bag hanger 114 is provided centrally above the walls 110 to allow fresh dialysate bags to be secured. Inside the space defined by the trapezoidal walls 110 is located the heating means shown in FIG. 2 at 74. The dialysate in the fresh dialysate bags is thus heated by conduction through the walls 110.

The electronic control means mentioned earlier with reference to FIG. 2 is provided in a housing shown at 116 in FIG. 3, the housing 116 being adapted to be received snugly within the space defined by the U-shaped portion 100, and to be fixed in place by a threaded fastener 118 adapted to be screwed upwardly through a bore 120 in the lower arm 98 of the U-shaped portion 100, and then into a threaded opening in the bottom of the housing 116 (not shown in FIG. 3). Power is supplied to the heater inside the trapezoidal walls 110 by way of a power cord 122 which is adapted to be plugged into the back of the housing 116. The portions inside the housing 116 are supplied with power through a further electrical cable 126, adapted to be plugged into a suitable wall receptacle.

Figure 5:
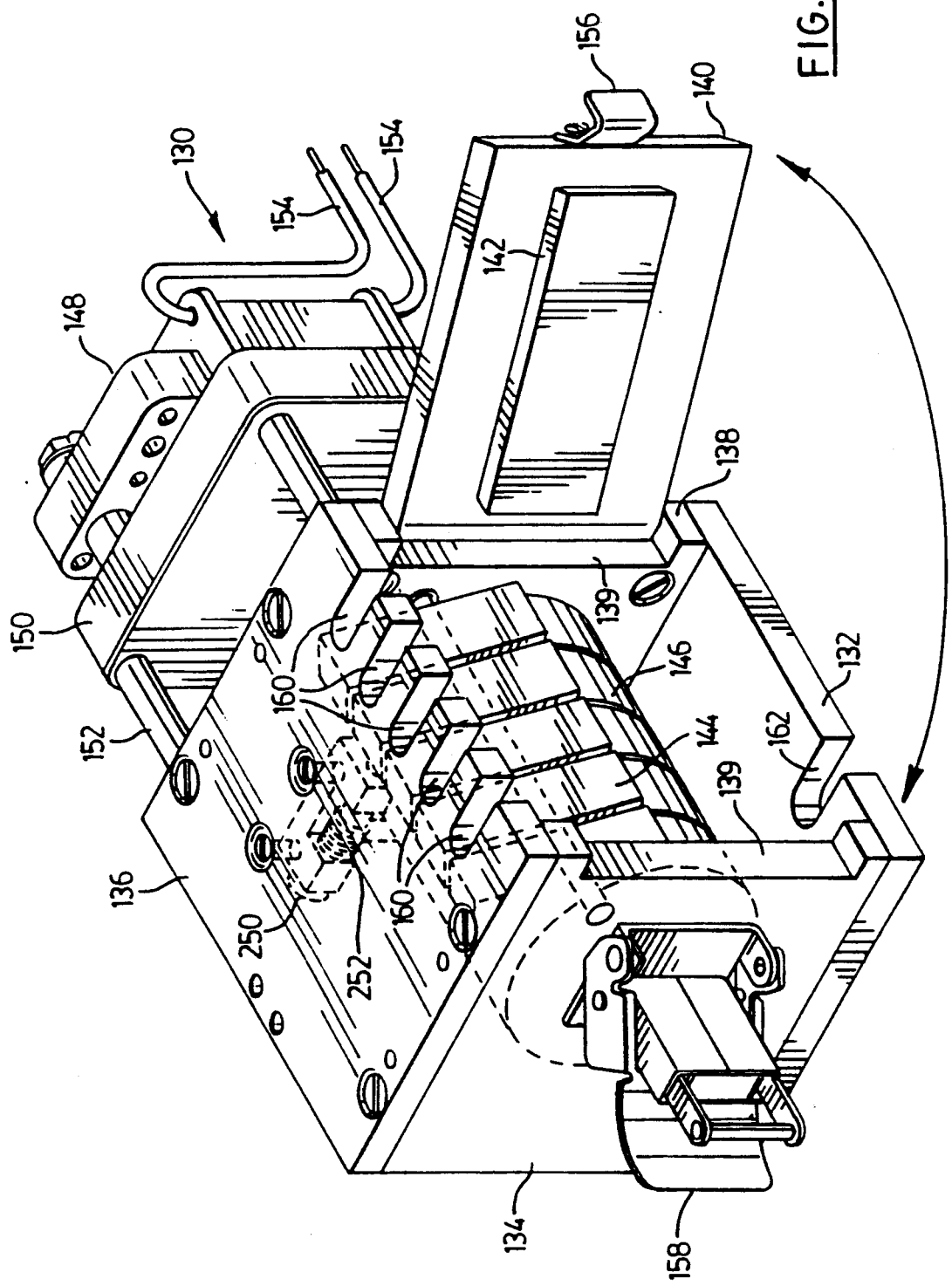

The housing 116 includes a clamping mechanism which is generally shown at 130 in FIG. 5. The mechanism shown in FIG. 5 is lodged within the housing 116 at the leftward forward corner thereof, as can be seen by comparing FIGS. 3 and 5. The mechanism 130 shown in FIG. 5 includes a bottom plate 132, a left side plate 134, a top plate 136 and a right side plate 138. The side plates 134 and 138 each have a central recess 139 for receiving a clamping door 140 which includes a rubber pad 142 adapted to cooperate with five clamping fingers 144, separately operable by individual cams 146 which are adapted to rotate simultaneously about a horizontal axis under the urging of an electric motor 148 acting through a speed reducer 150. Spacing pins 152 are provided to space the housing of the speed reducer 150 from the right side plate 138. The motor 148 is fed by electrical leads 154. As can be well seen in FIG. 5, the mechanism includes a catch 156 adapted to cooperate with a strike 158 in the usual manner, to secure the door in place against the recesses 139 in the forward vertical edges of the side plates 134 and 138.

The top plate 136 is provided with five slots 160, for receiving the conduits 78, 80, 82, 84 and 86. The position of the clamping fingers 144 is such as to ensure that they will be in a position to close their respective conduits (typically plastic tubes) so long as the conduits are received in the slots 160.

The bottom plate 132 has a further slot 162, which receives the conduit 76. The conduit 76 does not require to be closed off, with the result that, once connected, the peritoneum cavity of the patient is in continuous communication with the manifold 68.

In a preferred embodiment, the apparatus described herein requires the user to select three particular values or parameters, as follows:
  (a) Fill/Dwell Time: This can range from 0.0 minutes to 10 hours at 1 minute intervals;
  (b) Drain Time: This can range from 0.0 minutes to 99 minutes at intervals of 1 minute;
  (c) Solution Volume: This ranges from 0.1 liter up to 3.0 liters at 0.1 liter intervals.

The fill/dwell time determines the time the patient takes to receive and keep fresh dialysate for the actual dialysis process. The drain time is the time allowed for the patient to drain out the spent dialysate plus any excess fluid removed from the same patient. The solution volume setting tells the machine the size of the fresh dialysate bags being used. With this information, the machine calculates the minimum amount of fluid expected from the patient during drain. If this volume or a preset fraction of the volume is not attained during or at the end of the drain time, the drain alarm is activated and the machine does not switch to the next fill state.

Figure 4B:
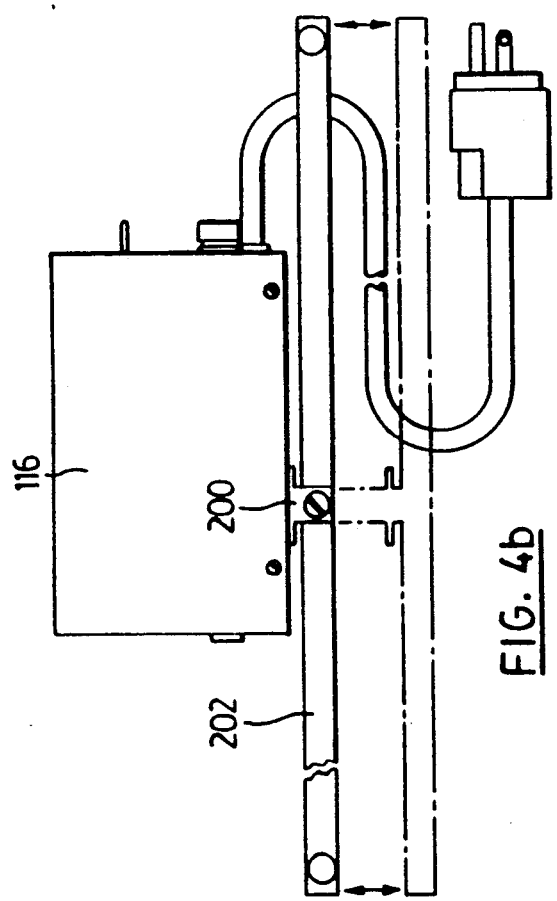
Figure 4A:
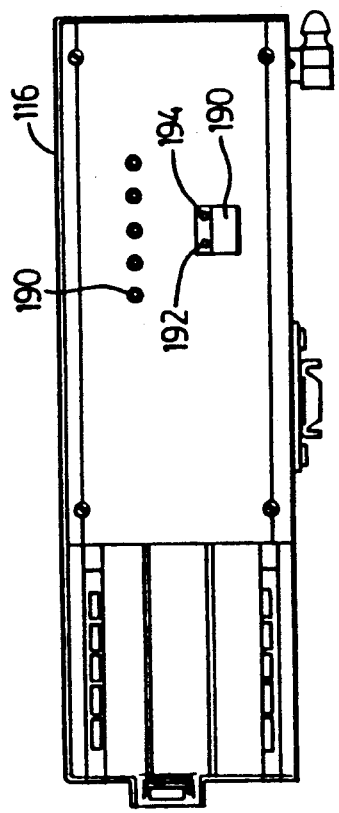
Figure 4C:
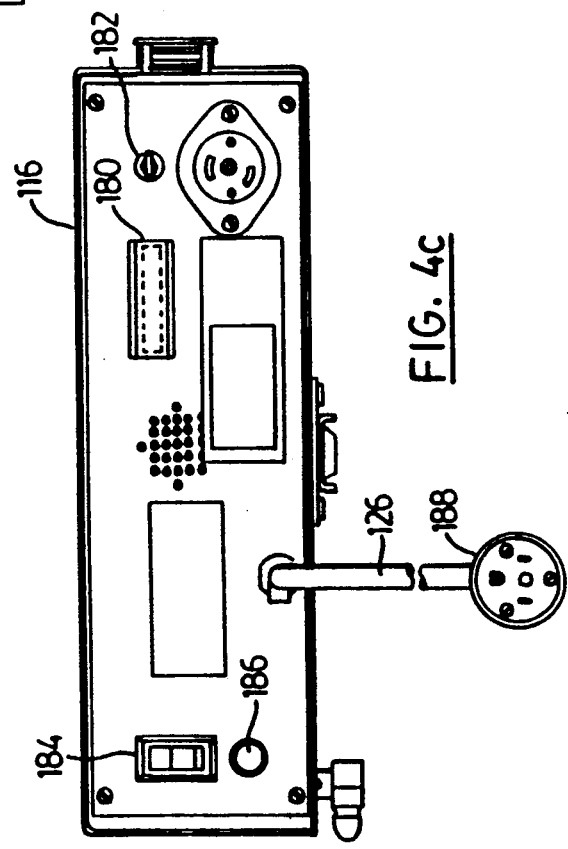

Attention is now directed to FIGS. 4a, 4b and 4c, which illustrate the housing 116 in three different elevational views.

In the rear view shown in FIG. 4c, a selection box 180 is provided to allow the user to select the three specific quantities mentioned immediately above. Specifically, the user selects the fill/dwell time in hours and minutes, the drain time in minutes, and the solution volume in liters. To the right of the box 180 is a switch 182 which allows the user to put the apparatus on either automatic cycling or manual operation. The manual operation will be described later in this specification.

At the left in FIG. 4c is a main power switch 184, and a fuse 186 is shown below the switch 184. FIG. 4c shows the power cord 126 and a power plug 188.

In FIG. 4a, showing the front view, a "start/advance" switch 190 is shown at lower right. LED's 192 and 194 above the switch 190 indicate whether the apparatus is in the drain phase or in the fill/dwell phase. Five LEDs (of which one is shown at 196) indicate which of the four dialysate bags 72 is in use.

As best seen in the side elevation of FIG. 4b, the housing 116 contains an electronic weighing mechanism from which downwardly extends a central vertical arm 200, to which is connected a horizontal weigh arm 202 from which the receptacle 70 (seen in FIG. 2) is adapted to be suspended.

Before describing in greater detail the mechanism connected with the balance arm 202 and the central arm 200, it is important to understand clearly a particular disadvantage of the prior art.

In the conventional cycler machine design, the weigh bag is capable of detecting a maximum of about 5 kg of drained dialysate from the patient. Hence the cycler machine weighs the drain bag (receiving the spent dialysate from the patient) during each drain mode and must empty the drain bag after each drain mode (i.e. during the fill and/or dwell mode). Because of this limitation the cycler tubing set cannot be made a "closed" system (i.e. it is opened to the final drain, with the possibility of bacterial back-tracking into the drain bag and the tubing set). This also contributes to the complexities of the cycler tubing sets and an excessive use of material. A novel approach for weighing the spent dialysate is used for the present invention.

Figure 7:
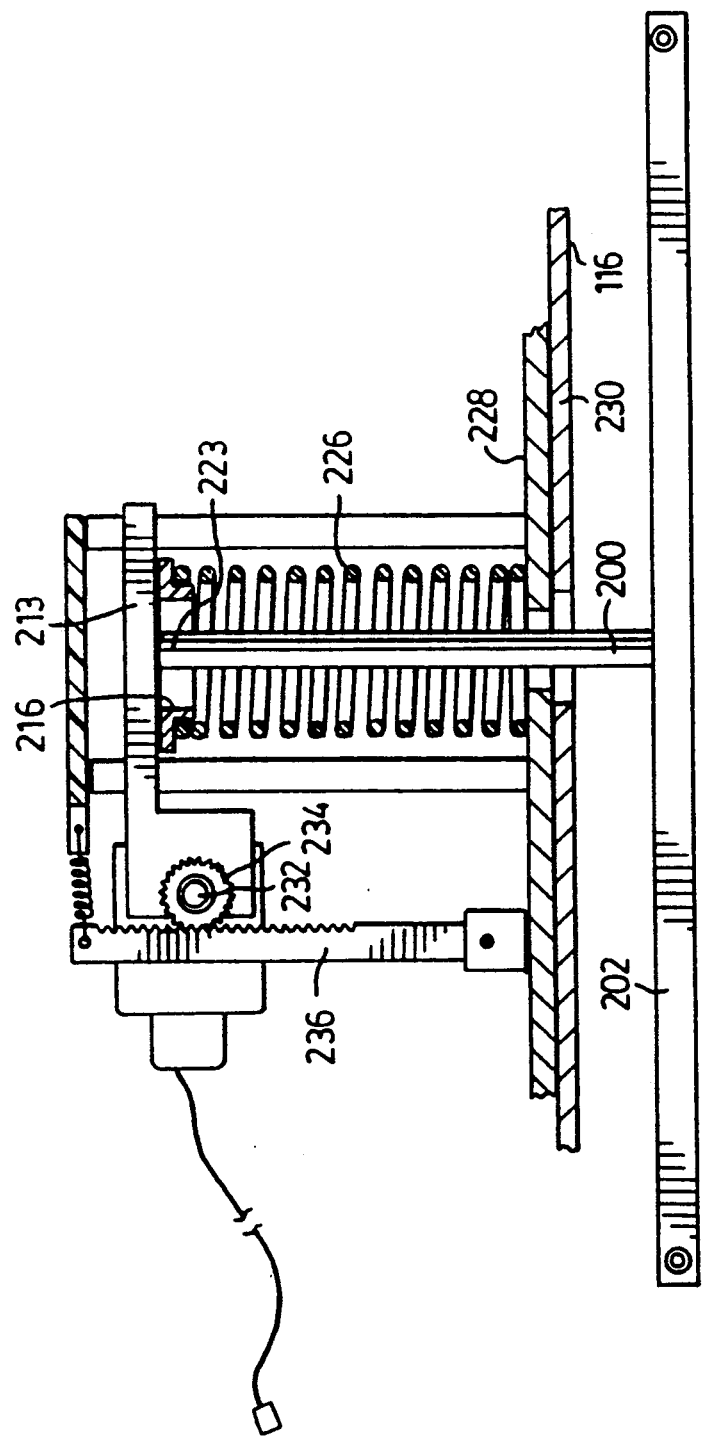

As previously mentioned, the receptacle 70 is suspended on the horizontal weigh arm 202 which is supported by the vertical arm 200. Referring to FIG. 7, the vertical arm 200 is connected at its upper end 223 to a horizontal support 213 which rests on a ring bushing 216. A helical compression spring 226 bears at its upper end against the ring bushing 216 and bears at the lower end against a plate 228 which rests upon a bottom wall 230 of the housing 116. Thus, the spring 226 continually presses upwardly against the ring bushing 216 and thus provides an upward force acting upon the horizontal weigh arm 202 in order to balance the weight of the receptacle 70 which the arm 202 suspends. The horizontal support 213 supports for rotation an optical encoder shaft 232, and a spur gear 234 is connected to the shaft 232 for rotation therewith. The spur gear 234 engages a vertical rack 236 which is fixed in place within the housing 116.

During the drain mode, the gradually increasing weight of the spent dialysate collecting in the receptacle 70 is transmitted to the spring 226 through the vertical arm 200, causing the spring 226 gradually to compress. The compression is in proportion to the applied weight, and as a result the horizontal support 213 travels downwardly. This causes the spur gear 234, moving with respect to the vertical rack 236, to rotate. The optical encoder translates the resulting rotation of the shaft 232 into electrical pulses which are transmitted to a microprocessor. This allows the microprocessor to register the weight of the drained dialysate contained in the receptacle 70 at any time.

The capacity of the weigh spring 226 limits the maximum weight which the microprocessor can detect through the weighing mechanism (a typical maximum limit is 15 kg). For this reason, the receptacle 70 does not have to be emptied after each drain mode. The closed receptacle 70 thus terminates the fluid path.

This unique weighing mechanism achieves the following benefits:
 (a) electronic control simplicity;
 (b) eliminates frequent field calibration of expensive transducers;
 (c) reduces electronic signal drifts;
 (d) eliminates scale zeroing;
 (e) provides easy machine service;
 (f) reduces cost of fabrication and maintenance.

It is evident from the previous description of FIG. 3 that all of the main components of the apparatus are centrally disposed about the common vertical axis of the first post portion 96 and the second post portion 104. This allows the base 90 to have the smallest possible dimensions, thus reducing the overall size and improving the manipulability and convenience of the apparatus.

Figure 8B:
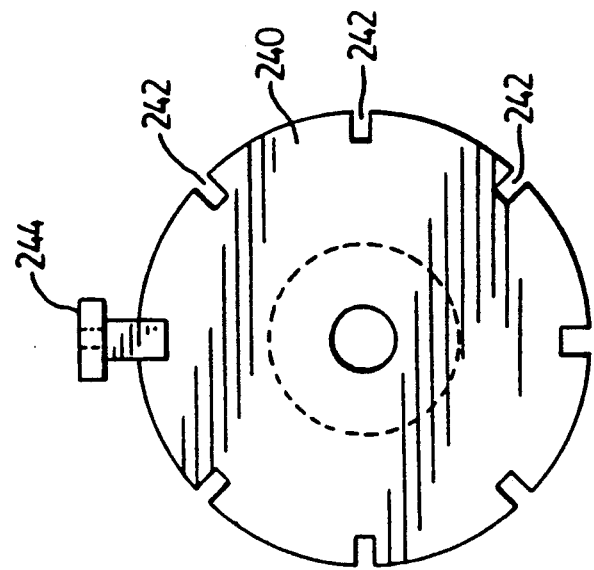
Figure 8A:
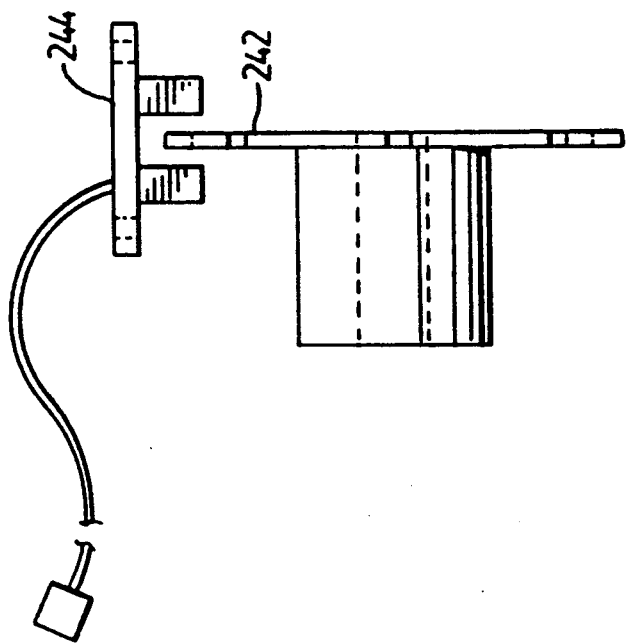

Before discussing the operation of this apparatus, it is appropriate to describe a further component of the mechanism shown in FIG. 5. A position sensor disc is attached to the shaft supporting the cams 146. The disc is not visible in FIG. 5, but it is shown in elevation in FIGS. 8a and 8b. As shown, the position sensor disc 240 has a plurality of short, radially directed, spaced-apart slots 242 in its periphery. The number of slots in the sensor disc 240 corresponds to the number of distinct stopping positions of the cam. For the illustrated embodiment, there are eight slots in the position sensor disc 240. As the motor 148 drives the shaft, the position sensor disc 240 rotates, with its periphery passing through an electronic optical switch 244. Whenever one of the slots 242 is aligned with the path of the optical switch, an electrical signal is generated and transmitted to the microprocessor, whereupon the microprocessor sends a signal to stop the motor 148. When the advance/start button 190 is depressed, the microprocessor starts the motor 148, which runs until the next slot 242 in the position sensor disc 240 becomes aligned with the optical switch 244. The microprocessor then stops the motor. Correct alignment of the slots with the cams will cause the tubing sets in the clamping block to be sequentially opened and closed.

Looking at FIG. 5, there is a microswitch (not illustrated) coupled to the movement of the forth clamping finger of the clamping system. When the fourth clamp is opened (i.e. at the fourth fill state) a plunger 250 is pushed forward by a plunger spring 252, thus opening the microswitch. The microswitch sends an electrical signal to the microprocessor, which uses this signal as an indexer (or a reference) and thereby identifies the rest of the clamping positions. This allows it to sequentially illuminate the position and state lights accordingly on the fact plate.

Operation

The operation of this apparatus is simply described. Firstly, the heater cord 122 is plugged into the housing 116, and the plug 188 is inserted into the wall. When the housing is turned on with the main power switch 184, a preliminary drain takes place to remove residual dialysate from the patient. After or simultaneously with this preliminary drain, the fresh dialysate bags (presumed to have been hung on the support/heater shown at the top in FIG. 3) are heated. Until they reach the required temperature, the apparatus will not perform the dialysis.

However, once the temperature is reached, the user can select either the automatic cycling or the manual cycling, using the switch 182 on the back of the housing. Assume that automatic cycling is chosen. Then, on the front of the housing, the switch 190 allows the user to start the procedure.

As previously described, there are two independent states of operation: the fill/dwell phase and the drain phase. During the fill/dwell phase, one of the tubing sets leading to the fresh dialysate bags is opened by the operation of the appropriate cam 146 and its effect on the corresponding clamping fingers 144. All the other tubing sets including the set connected to the receptacle 70 are firmly closed, with the exception of conduit 76 leading to the patient. Then, the heated dialysate connected to the open tubing set is completely emptied into the patient. The dialysate remains inside the patient for a preset time, as determined by the fill/dwell time setting. At the end of the fill/dwell time, the drain phase commences, in which all of the tubing sets leading to the fresh dialysate bags are closed. Only the tubing set leading to the receptacle 70 is open (and of course the conduit to the patient is also open). In this state, the peritoneum cavity 64 of the patient 62 drains the spent dialysate out into the receptacle 70. By the end of the drain time (determined by the drain time setting), if the patient fails to drain out a predetermined minimum volume of the spent dialysate into the receptacle 70, an alarm is activated. If the alarm is activated, the apparatus will not switch into the next fill/dwell phase. If, however, there is no drain alarm, the machine will advance to the next fill/dwell phase to allow another fresh dialysate bag to empty its contents into the peritoneum cavity 64 of the patient 62. Next, the machine automatically enters the drain phase. The above cycle is repeated until the contents of all the fresh dialysate bags are individually and selectively used up. In a preferred mode, the automatic action is halted after the contents of the last dialysate bag are emptied into the patient. At the end of the fill/dwell time, the patient has the option of either keeping the last dialysate volume or draining it out.

Again in a preferred embodiment, during the automatic mode of operation, should any alarm condition be encountered in any of the drain states, the machine initiates audible and visual alarms and does not advance to the next fill/dwell phase unless the alarm condition is corrected.

As previously mentioned, the apparatus can be operated in both an automatic and a manual mode.

In the manual mode the same initial parameter settings are selected namely the fill/dwell time, the drain time and the "solution volume" (volume of each fresh dialysate bag).

When first switched on, the machine initially enters a drain state to allow any excess fluid in the peritoneum cavity to be drained away prior to the initiation of the new dialysis cycle. At the end of this initial drain, which can be a fraction or all of the time selected as "drain time", the machine sounds an audible "end-of-state" condition. The user then depresses the "advance" switch 190 (FIG. 4a) to put the apparatus into the first fill/dwell phase. It is assumed that the fresh dialysate bags have by now been heated up to the required temperature. The contents of the first dialysate bag are then passed into the patient, and at the end of the fill/dwell time the audible "end-of-state" warning is again sounded. Depressing the "advance" switch again causes the apparatus to advance to the next drain state. This is repeated until all of the PD solution bags are used up and drained out respectively.

However, just as in the automatic mode, if a drain alarm condition arises during any drain phase, the machine cannot enter the next fill/dwell phase until the alarm condition is corrected.

It is to be pointed out that a major advantage of the present invention over the previous peritoneal dialysis machines, such as that described with respect to FIG. 1, is that it does not mix the contents of the fresh dialysate bags. It selects the dialysate bags individually during operation. This allows individual ones of the dialysate bags to be medicated with different drugs, and possibly incompatible drugs. Because of these unique characteristics, the apparatus of the present invention is relatively small, easy to operate and very versatile. Further, it requires less tubing set components and only minimum alarm provisions.

In the automatic mode the apparatus of this invention is used for IPD and CCPD treatments. In the manual mode, it is used for manual PD, intensive care PD, and CAPD treatments.

Intensive Care

This new PD machine makes it possible to medicate each bag separately with incompatible drugs. It also allows for the administration of different medications to patients at different times. This is ideal for treating patients with infections (peritonitis). The solution bags can be selectively medicated with antibiotics, thus substantially reducing the cost of operations.

Manual PD

Because the solution bags are selectively used by this new machine it is easy to alternate dialysate bags with different dextrose strengths. The machine can be used for patients with new catheters. It can be used for PD "lavage" of patients with peritonitis. The use of a machine reduces infection rate. By eliminating routine manual operations, the machine will also save the clinical staff valuable time. Therefore more quality time can be devoted to direct patient care.

CAPD

Because this new machine selects individual solution bags it lends itself ideally to CAPD. In manual mode the fill/dwell time could be set to between 4 and 6 hours as required by regular CAPD dwell time. By using a unique quick connect cap (U.S. Pat. No. 4,983,161, issued on Jan. 8, 1991, to Joseph E. Dadson, et al), the patient can safely disconnect from the tubing set after a fill in each fill/dwell state. By using this invention one can achieve the preferred "Flush-Before-Fill" condition which is claimed to reduce the peritonitis rate in PD.

With the apparatus of this invention and the simplicity of its associated tubing sets, the total daily cost of disposable sets is much less than that of current CAPD disposable "Y" sets. Since this machine heats up and maintains the dialysate at an ideal body temperature, the efficiency of CAPD dialysis (which is dependent on temperature) is greatly improved.

For CAPD the new PD machine is set up only once in the day, preferably in the morning. Then the connections and disconnections are quickly made for each fluid exchange. Consequently this will:

(1) eliminate current patient fatigue;
(2) make it easier for elderly patients, with assistance for initial set-up, to do their own treatments;
(3) reduce the current four CAPD home nursing visits by clinical staff (or Victorian Order of Nurses) to only one, thereby reducing the home visit cost by more than one-half;
(4) make it possible for adolescent CAPD patients to safely perform their own dialysis exchanges after the initial set-up by their parents. This will give the adolescents the needed self-esteem and some degree of independence.

It should be noted here that with this invention each time that a CAPD patient is connected back to the tubing set, a "drain" is carried out first, thereby flushing the set to remove possible bacterial contamination before the patient fills again with dialysate. Thus the peritonitis rate will be greatly reduced in the CAPD procedure.

IPD and CCPD

The differences between CCPD and IPD are only
(i) the length of dwell time;
(ii) the number of dialysis exchanges per week, and
(iii) the time of operation (i.e. CCPD is done mostly at night).

This new apparatus therefore is suitable to be used for these two types cf PD modalities, because it is an APD machine.

By using this apparatus, for the first time ever a CAPD patient will be able to alternate between CAPD and CCPD. Above all, by using the combination of CAPD by day and CCPD by night, a home patient can have extended treatment within a 24-hour day period. As a result, patients will be able to perform their dialysis treatments every other day. Hence, a CAPD patient may be able to have more "quality" time to spend with the rest of the family or to undertake special projects or assignments or pursue an occupation during non-dialysis days.

This apparatus thus makes it possible for clinicians to provide prescribed PD treatment (Manual PD, CAPD, CCPD or IPD) to their patients, with higher efficiency, lower cost and simplicity.

Figure 6:
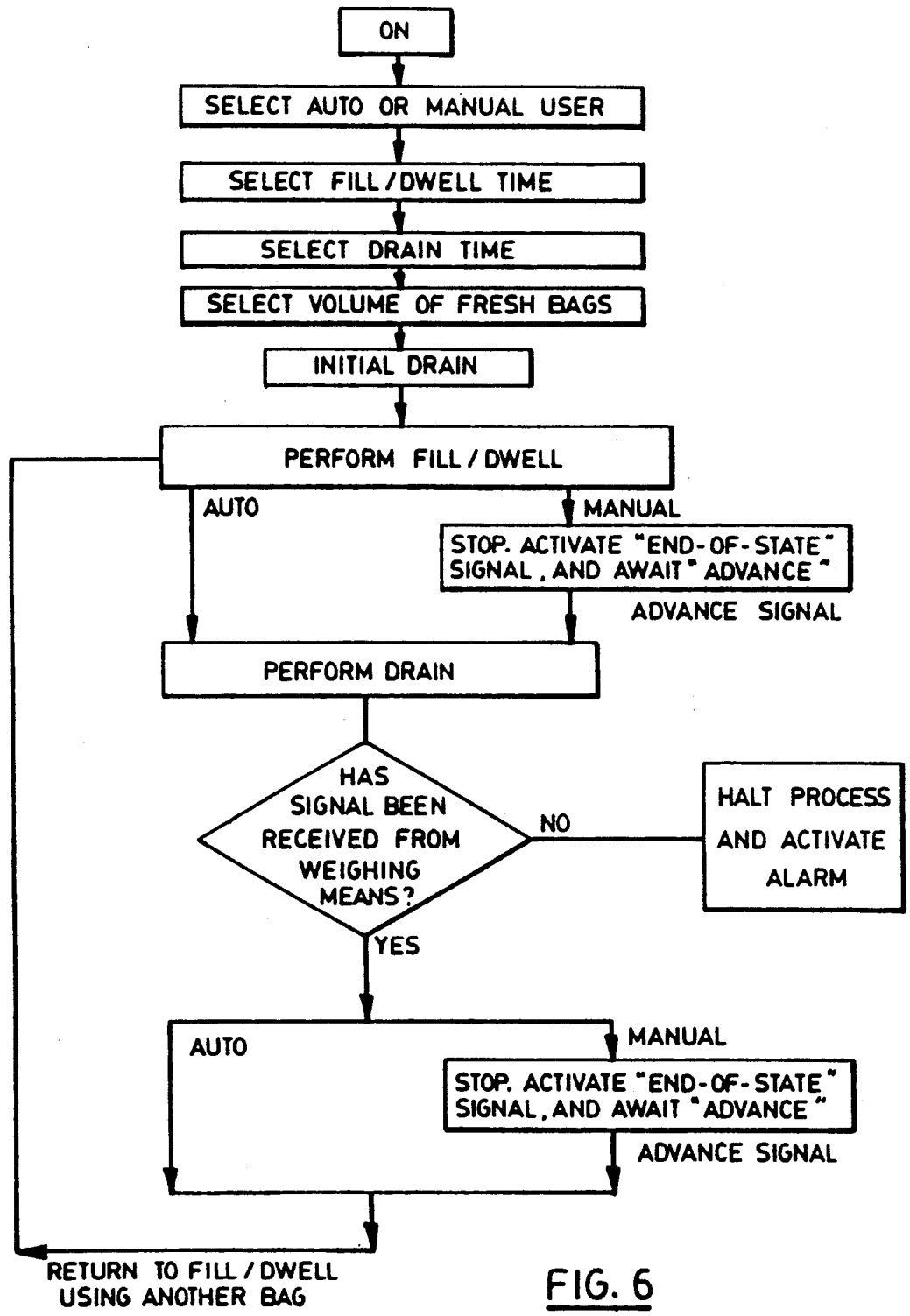

Attention is now directed to FIG. 6, which shows a logic flow diagram for use by a microprocessor or equivalent unit contained within the housing 116.

At the top of FIG. 6, the first block shows the apparatus being turned on. Then follows the selection of automatic or manual operation, the selection of the fill/dwell time, the selection of the drain time, and the selection of the quantity of liquid contained in each fresh dialysate bag. Depressing the "start" 190 (FIG. 4a) starts the initial drain, with the purpose of removing any left-over fluid in the peritoneum cavity of the patient. The drain time can be that selected or a fraction thereof.

Assuming automatic cycling, the apparatus then performs the fill/dwell phase, and then goes automatically to the drain phase. By contrast, if manual operation has been selected, the apparatus will stop after the fill/dwell phase, activate the "end-of-state" signal, and await the pushing of the "advance" button. When the latter occurs, the apparatus then goes to the drain phase.

At the end of the drain phase, the logic asks whether a signal has been received from the weighing means. If the answer is no, it means that insufficient fluid has drained from the patient, and the result is to halt the process and to activate an audible and/or visual alarm.

If the answer is yes, then the procedure is normal and, on automatic cycling, the apparatus will immediately return to the fill/dwell phase using another fresh dialysate bag. This returns the logic along arrow 203 to the first performance of the fill/dwell phase.

However, on manual operation, the apparatus will stop after the drain has been performed, activate the "end-of-state" signal, and await the pressing of "advance" button. Upon the pressing of that button, the apparatus will then return to the fill/dwell phase using the next fresh dialysate beg.

The looping back along the arrow 203 is allowed to occur only three time, thus using up all four bags. Naturally, if the apparatus is designed to incorporate more or less bags than four, the permissible looping back along arrow 203 would be different.

While one embodiment of this invention has been illustrated in the accompanying drawings and described hereinabove, it will be evident to those skilled in the art that changes and modifications may be made therein, without departing from the essence of this invention as set forth in the appended claims.

The embodiments of the invention in which an exclusive property or privilege is claimed are defined as follows:

1. A method for carrying out peritoneal dialysis on a patient whose peritoneum cavity communicates with a patient catheter, the method comprising the steps:
    a) providing an apparatus which includes
        a manifold,
        a receptacle for waste dialysate,
        support means for supporting a plurality of fresh dialysate bags,
        heating means for heating dialysate bags on said support means,
        a first conduit for connecting the manifold with the patient catheter,
        a second conduit for connecting said manifold with said receptacle,
        at least two further conduits for connecting the manifold individually with a plurality of fresh dialysate bags, and
        clamping means for selectively closing said conduits;
    b) using electronic control means for controlling said clamping means in an automatic mode in which the control means causes the apparatus to cycle through the following phases:
        1) a fill/dwell phase in which, for a first predetermined time, the first conduit and one of said at least two further conduits are both open while the remaining conduits are closed, whereby dialysate enters the patient's peritoneum cavity by gravity and remains there, so long as the vertical level of the dialysate bags is above that of the patient, and
        2) a drain phase in which, for a second predetermined time, the first and second conduits are both open while the remaining conduits are closed, whereby waste dialysate drains by gravity from the patient's peritoneum cavity to said receptacle, so long as the vertical level of the patient is above that of the receptacle,
    c) determining whether a sufficient quantity of dialysate has drained from the patient's cavity during the drain phase, and passing such information to said electronic control means, the electronic control means being such as not to advance to the next fill/dwell phase if an insufficient quantity of dialysate has drained, and
    d) repeating said steps 1) and 2) for another fresh dialysate bag, and so on until all such bags have been used.

2. The method claimed in claim 1, in which step c) is carried out by monitoring the weight of said receptacle and its contents.

3. An apparatus for carrying out peritoneal dialysis on a patient whose peritoneum cavity communicates with a patient catheter, the apparatus comprising:
    (1) a manifold,
    (2) a receptacle for waste dialysate,
    (3) a plurality of fresh dialysate bags,
    (4) support means supporting said plurality of fresh dialysate bags,
    (5) heating means for heating said dialysate bags on said support means,
    (6) a first conduit for connecting the manifold with the patient catheter,
    (7) a second conduit for connecting said manifold with said receptacle,
    (8) at least two further conduits connecting the manifold individually with each of said fresh dialysate bags,
    (9) clamping means for selectively closing at least said second and said further conduits, and
    (10) electronic control means for controlling said clamping means, the electronic control means having an automatic mode in which the control means causes the apparatus to cycle through the following phases:
        a) a fill/dwell phase in which, for a first predetermined time, the first conduit and one of said at least two further conduits are both open while the remaining conduits are closed, thus allowing dialysate to enter the patient's peritoneum cavity by gravity and remain there, so long as the vertical level of the dialysate bags is above that of the patient, and
        b) a drain phase in which, for a second predetermined time, the first and second conduits are both open while the remaining conduits are closed, thus allowing waste dialysate to drain by gravity from the patient's peritoneum cavity to said receptacle, so long as the vertical level of the patient is above that of the receptacle, said steps a) and b) repeating for another fresh dialysate bag, and so on until all such bags have been used;

(11) safety means for determining whether a sufficient quantity of dialysate has drained from the patient's peritoneum cavity during the drain phase, and for passing such information to said electronic control means, said electronic control means being such as not to advance to the next fill/dwell phase if an insufficient quantity of dialysate has drained, and

(12) selection means allowing a user to select the first and second predetermined times.

4. The apparatus claimed in claim 3, in which said safety means includes weighing means for weighing said receptacle and for supplying a signal when the weight of the receptacle exceeds a predetermined amount, and means for passing said signal to said electronic means, the apparatus further including:

(13) further selection means allowing the user to input the quantity of liquid in a fresh dialysate bag, said electronic control means being programmed to calculate, from such input, the amount of waste dialysate to expect from the patient during the drain phase.

5. The apparatus claimed in claim 4, further comprising:

a suspension means which includes a horizontally displaceable base portion, a first vertical post portion having a lower end and an upper end, said lower end being affixed to said base portion, a U-shaped intermediate portion secured to the upper end of said post portion, the U-shape having two arms and a bottom, the bottom of the U-shape being displaced laterally from said post portion, and a second vertical post portion fixed to said U-shaped portion in substantial vertical alignment with said first post portion, the second post portion supporting said support means, and a control housing which contains said clamping means, said weighing means and said electronic control means, the housing being located within said U-shaped portion, whereby the weights of all the components of the apparatus act generally along the common axis of the vertical post portions, thus permitting the base portion to have a minimal lateral extent.

6. The apparatus claimed in claim 3, further comprising:

a suspension means which includes a horizontally displaceable base portion, a first vertical post portion having a lower end and an upper end, said lower end being affixed to said base portion, a U-shaped intermediate portion secured to the upper end of said post portion, the U-shaped having two arms and a bottom, the bottom of the U-shape being displaced laterally from said post portion, and a second vertical post portion fixed to said U-shaped portion in substantially vertical alignment with said first post portion, the second post position supporting said support means, a control unit housing said clamping means and said electronic control means, and being located within said U-shaped portion, whereby the weights of all the components of the apparatus act generally along the common axis of the vertical post portions.

7. The apparatus claimed in claim 3, in which said safety means includes:

a hanger for suspending said receptacle, a support means, biasing means operatively interconnecting said hanger and said support means such that, as the receptacle increases in weight, the hanger descends with respect to said support means, and rack-and-pinion means operatively interconnected between said hanger and said support means and including a rack with teeth and a pinion with teeth, the rack teeth engaging the pinion teeth, whereby as the hanger descends the pinion rotates, and electronic detection means for detecting rotation of said pinion and for transmitting to said electronic control means information based on such pinion rotation.

8. The apparatus claimed in claim 7, in which said biasing means includes a coil compression spring.

9. The apparatus claimed in claim 7, in which said hanger is a horizontal member, a vertical member connected to said horizontal member, a vertical member connected to said horizontal member at an intermediate location thereon and extending upwardly therefrom, a horizontal support connected to the vertical member adjacent the top of the latter, a coil compression spring surrounding the vertical member, the spring urging the horizontal support upwardly with respect to said support means; and in which said pinion is mounted to said horizontal support for free rotation with respect thereto, such that the pinion moves vertically along with the horizontal support, the rack being fixed with respect to the support means.

10. The apparatus claimed in claim 3, in which the electronic control means further has a manual mode in which the electronic control means stops after each phase, and will not initiate a new phase until it receives a manual instruction to advance.

* * * * *